(12) United States Patent
Ishiguro et al.

(10) Patent No.: US 7,862,697 B2
(45) Date of Patent: Jan. 4, 2011

(54) SENSOR CONTROL DEVICE

(75) Inventors: Yasuhiro Ishiguro, Aichi (JP); Shinji Kumazawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 750 days.

(21) Appl. No.: 11/592,194

(22) Filed: Nov. 3, 2006

(65) Prior Publication Data
US 2007/0151849 A1      Jul. 5, 2007

(30) Foreign Application Priority Data
Nov. 4, 2005      (JP) ............................. 2005-320916

(51) Int. Cl.
*G01N 27/407* (2006.01)
(52) U.S. Cl. .................. 204/406; 204/425; 205/781
(58) Field of Classification Search ............... 204/406, 204/425; 205/781, 784; 73/23.31
See application file for complete search history.

(56) References Cited
U.S. PATENT DOCUMENTS
6,120,663 A      9/2000   Kato et al.

2004/0089055 A1*  5/2004  Cramer et al. ............. 73/23.32
2004/0238378 A1* 12/2004  Kumazawa et al. ......... 205/781

FOREIGN PATENT DOCUMENTS
WO       WO 03/083465 A1      10/2003

* cited by examiner

*Primary Examiner*—Kaj K Olsen
(74) *Attorney, Agent, or Firm*—Sughrue Mion, PLLC (57) ABSTRACT

A sensor control device, and a gas sensor and sensor control device for applying a voltage to a sensor element of the gas sensor including an oxygen ion conductor and a pair of electrodes formed on the oxygen ion conductor of the gas sensor. The sensor control device includes a potential output terminal electrically connected to one of the pair of electrodes and a potential reference terminal electrically connected to the other of the pair of electrodes constituting the sensor element. The sensor control device applies a target voltage to the sensor element via the potential output terminal, corrected to take into account variation in the potential of the potential reference terminal.

11 Claims, 3 Drawing Sheets

SENSOR CONTROL DEVICE

BACKGROUND OF THE INVENTION

1. Field of the Invention

The present invention relates to a sensor control device provided with a potential reference terminal and a potential output terminal, the sensor control device applying a voltage to a sensor element connected between the potential reference terminal and the potential output terminal.

2. Description of the Related Art

A sensor control device provided with a potential reference terminal and a potential output terminal has been used to apply a voltage to a sensor element connected between the potential reference terminal and the potential output terminal.

An example of such a sensor control device is an NOx sensor control device that applies a voltage to an NOx sensor as disclosed in WO03/083465 (FIG. 1 and FIG. 8).

The NOx sensor control device applies a voltage to the NOx sensor element (Ip2 cell) connected between the potential reference terminal (Vcent terminal) and the potential output terminal (Ip2 terminal) by setting the potential of the potential reference terminal (Vcent terminal) to be a reference point target potential, and by setting the potential of the potential output terminal (Ip2 terminal) to be an output point target potential.

Both the reference point target potential and the output point target potential are set in such a manner that the voltage applied to the NOx sensor element (Ip2 cell) remains at the target-applied voltage.

In the sensor control device in the related art, however, even in the case where the potential of the potential output terminal (Ip2 terminal) is set to be the output point target potential at a high degree of accuracy, there is a possibility that the actual voltage applied to the sensor element assumes a voltage value different from the target applied voltage. This can occur when the potential of the potential reference terminal (Vcent terminal) fluctuates due to influence of noise or the like.

More specifically, because the sensor control device in the related art is configured so that the potential of the potential terminal (Ip2 terminal) and the potential of the potential reference terminal (Vcent terminal) are independently controlled, a problem arises in that even when the potential of the potential output terminal (Ip2 terminal) is set at a high degree of accuracy, the voltage applied to the sensor element varies when the potential of the potential reference terminal (Vcent terminal) fluctuates.

SUMMARY OF THE INVENTION

The invention was made in view of the foregoing problems, and an object thereof is to provide a sensor control device capable of suppressing fluctuation of the voltage applied to the sensor element connected between the potential reference terminal and the potential output terminal even when the potential of the potential reference terminal fluctuates.

The above objective is achieved in a first aspect of the invention by providing a sensor control device including a potential reference terminal and a potential output terminal, said sensor control device being adapted for applying a voltage to a sensor element having an oxygen ion conductor and a pair of electrodes formed on the oxygen ion conductor and for connecting the potential reference terminal to one of the pair of electrodes and the potential output terminal to the other of the pair of electrodes, said sensor control device comprising:

a reference potential setting section for setting the potential of the potential reference terminal to a reference point target potential;

an output potential setting section for setting the potential of the potential output terminal to an output point target potential so that a target voltage is applied to the sensor element with reference to the potential of the potential reference terminal set to the reference point target potential; and an output point potential correction section for correcting the output point target potential according to fluctuation in the potential of the potential reference terminal from the reference point target potential, so that the voltage applied to the sensor element remains at the target applied voltage, said output potential setting section adjusting the potential of the potential output terminal so as to assume the corrected output point target potential.

More specifically, the sensor control device is configured to correct the output point target potential in response to the extent of fluctuation in potential between the actual potential of the potential reference terminal and the reference point target potential, and to set the potential of the potential output terminal so to assume the corrected output point target potential. In this manner, the voltage applied to the sensor element remains at the target applied voltage.

By correcting the output point target potential in response to the extent of fluctuation in potential of the potential reference terminal as described above, the sensor control device is able to markedly suppress deviation in the voltage applied to the sensor element from the target applied voltage. This is the case even when the actual potential of the potential reference terminal fluctuates due to the influence of noise and the like.

Hence, according to the invention, even when the potential of the potential reference terminal fluctuates, it is possible to suppress fluctuation in the voltage applied to the sensor element connected between the potential reference terminal and the potential output terminal.

In the case where the potential of the potential reference terminal is higher than the reference point target potential, the output point potential correction section is able to correct the potential of the potential output terminal by raising the potential of the potential output terminal above the output point target potential by a quantity corresponding to the increase in potential (the amount of fluctuation in potential) of the reference point target potential. Conversely, in the case where the potential of the potential reference terminal is below the reference point target potential, the output point potential correction section is able to correct the potential of the potential output terminal by lowering the potential of the potential output terminal below the output point target potential by a quantity corresponding to the decrease in potential of the reference point target potential.

The above object is also achieved in a second aspect of the invention by providing a gas sensor and a sensor control device for applying a voltage to a sensor element of the gas sensor, said gas sensor comprising:

a first measurement chamber into which a gas to be measured is introduced via a first diffusion resistor portion;

a first oxygen ion pump cell comprising a first oxygen ion conductor and first and second electrodes formed on the first oxygen ion conductor so that the first electrode is arranged in the first measurement chamber for pumping oxygen into or out of the gas to be measured that has been introduced into the first measurement chamber;

a second measurement chamber into which the gas to be measured after having been acted on in the first measurement chamber is introduced via a second diffusion resistor portion;

a second oxygen ion pump cell comprising a second oxygen ion conductor and third and fourth electrodes formed on the second oxygen ion conductor so that the third electrode is arranged in the second measurement chamber, wherein a current corresponding to the concentration of a particular gas in the second measurement chamber flows in the second oxygen ion pump cell;

a reference oxygen chamber set to have a reference oxygen partial pressure atmosphere; and an oxygen partial pressure detection cell comprising a third oxygen ion conductor and fifth and sixth electrodes formed on the third oxygen ion conductor so that the fifth electrode is arranged in the first measurement chamber and the sixth electrode is arranged in the reference oxygen chamber;

said sensor control device comprising a potential output terminal and a reference output terminal electrically connected to said third and fourth electrodes of the second oxygen ion pump cell, respectively, or to said fifth and sixth electrodes of the oxygen partial pressure detection cell, respectively, said sensor control device further comprising:

a reference potential setting section for setting the potential of the potential reference terminal to a reference point target potential;

an output potential setting section for setting the potential of the potential output terminal to an output point target potential so that a target voltage is applied to the sensor element with reference to the potential of the potential reference terminal set to the reference point target potential; and an output point potential correction section for correcting the output point target potential according to fluctuation in the potential of the potential reference terminal from the reference point target potential, so that the voltage applied to the sensor element remains at the target applied voltage, said output potential setting section adjusting the potential of the potential output terminal so as to assume the corrected output point target potential.

In the gas sensor element having two oxygen ion pump cells and two measurement chambers, the current flowing into the second oxygen ion pump cell is extremely small. Hence, even when the potential of the potential reference terminal used as a reference of the applied voltage to the second oxygen ion pump fluctuates to a small extent, current flowing into the second oxygen ion pump cell does fluctuate, which current fluctuation can significantly deteriorate the measurement accuracy of the concentration of a particular gas.

By making the second oxygen ion pump cell in the gas sensor element the sensor element to which a voltage is applied in the sensor control device of the invention, which is a preferred embodiment of the invention, it is possible to suppress fluctuation in the voltage applied to the second oxygen ion pump cell, which can in turn enhance the detection accuracy of the concentration of a particular gas.

The sensor control device may be configured such that the output point potential correction section comprises a non-inverting amplifier circuit, and the potential of the potential reference terminal is applied to the input of the non-inverting amplifier.

By configuring a non-inverting amplifier circuit comprising an analog circuit as the output point potential reference correction section, it is possible to achieve an inexpensive circuit capable of correcting the output point target potential with a proper response to fluctuation in the potential of the potential reference terminal.

The sensor control device may be provided with plural potential output terminals, in which case plural output potential setting sections and output point potential correction sections are provided corresponding to respective plural potential output terminals.

By providing plural potential output terminals, output potential setting sections, and output point potential correction sections, not only is it possible to apply a voltage to the respective components of a sensor element that require an external voltage, but it is also possible to suppress fluctuation in the value of the voltage applied to the respective components induced by a fluctuation at the potential reference terminal.

Hence, according to the invention, even when the potential of the potential reference terminal fluctuates, it is possible to suppress fluctuation in voltage applied to each of the plural components.

DESCRIPTION OF THE PREFERRED EMBODIMENTS

Hereinafter, an embodiment of the invention will be described with reference to the drawings. However, the present invention should not be construed as being limited thereto.

Figure 1:
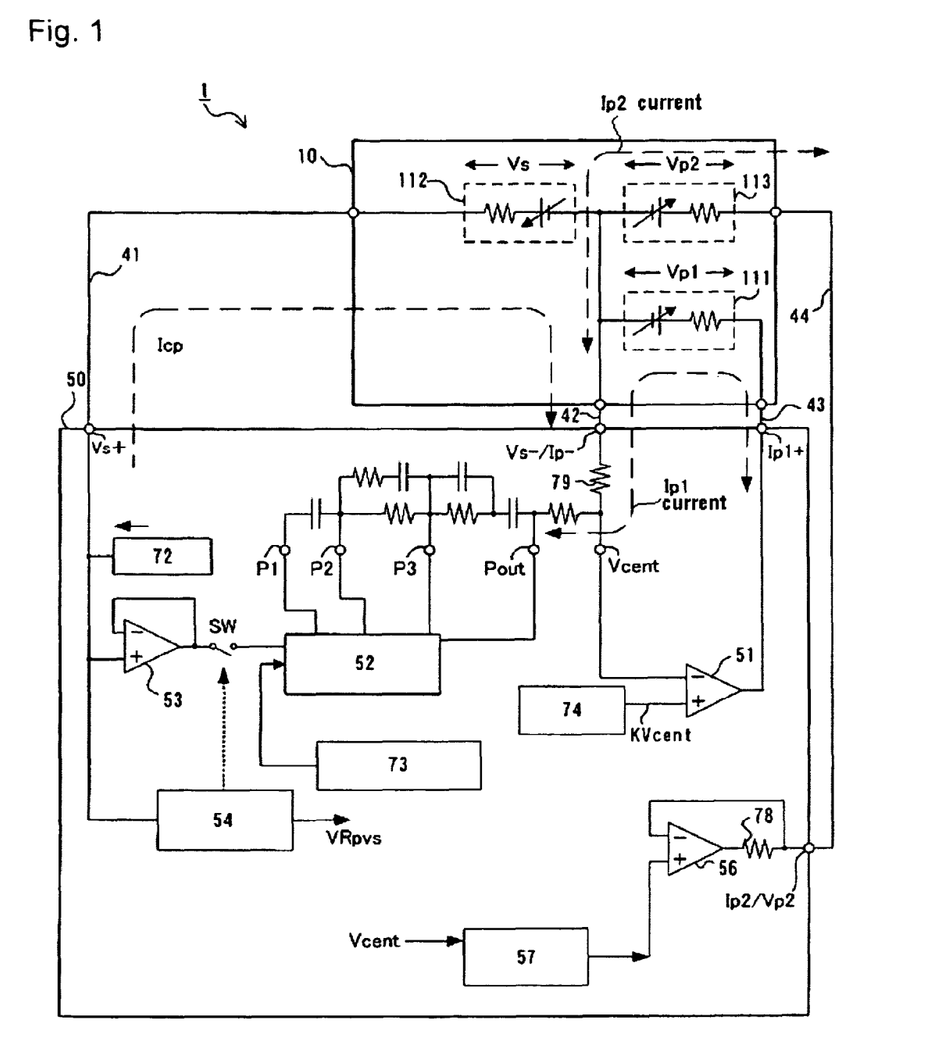
FIG. 1 is a view schematically showing the configuration of an NOx detection device provided with a sensor control device according to the invention.

FIG. 1 is a view schematically showing the configuration of an NOx detection device 1 provided with a sensor control device 50 to which the invention is applied.

The NOx detection device 1 is used to detect a particular gas (NOx in this embodiment) in the exhaust gas of an internal combustion engine (engine). The NOx detection device 1 includes a gas sensor element 10 and the sensor control device 50 as well as an unillustrated heater and heater control circuit.

The sensor control device 50 not only carries out energization control of the gas sensor element 10, but also detects a sensor signal. The heater heats the gas sensor element 10 to maintain it at the operating temperature (in other words, the activation temperature), and the heater control circuit carries out energization control for the heater.

The gas sensor element 10 is a sensor element for detecting NOx, and includes a first pump cell 111, an oxygen concentration detection cell 112, and a second pump cell 113.

The gas sensor element 10 is heated to the activation temperature by the heater provided separately.

Figure 2:
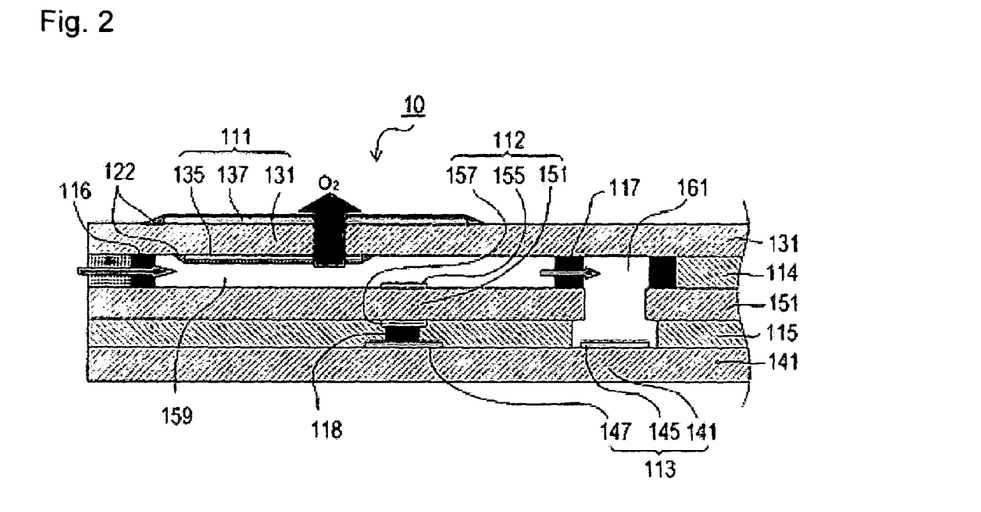
FIG. 2 is a cross section showing the internal configuration of a gas sensor element.

FIG. 2 is a cross section showing the internal configuration of the gas sensor element 10.

The gas sensor element 10 has a structure in which the first pump cell 111, the oxygen concentration detection cell 112, and the second pump cell 113 are laminated via insulation layers 114 and 115 primarily made of alumina, and includes a first measurement chamber 159 into which a gas to be measured is taken via a first diffusion resistor 116 made of porous alumina.

The gas sensor element 10 is able to pump oxygen into and out of the first measurement chamber 159 by means of the first pump cell 111. It is configured such that the oxygen concentration detection cell 112 is able to measure the difference between the oxygen concentration of a reference oxygen chamber 118 in which the oxygen concentration is controlled to be constant and that of the first measurement chamber 159 (that is, the oxygen concentration in the interior of the first measurement chamber 159).

The first pump cell 111 comprises a first solid electrolyte layer 131 made of zirconia having oxygen ion conductivity, and a first electrode 135 and a second electrode 137 disposed to sandwich the first solid electrolyte layer 131. The first electrode 135 and the second electrode 137 are made of platinum or platinum alloy, and a protection layer 122 made of a porous material is formed on the surface of each electrode.

The second pump cell 113 comprises a second solid electrolyte layer 141 made of zirconia having oxygen ion conductivity, and a third electrode 145 and a fourth electrode 147 disposed on the second solid electrolyte layer 141 at the surface facing the insulation layer 115. The third electrode 145 and the fourth electrode 147 are made of platinum or platinum alloy.

The oxygen concentration detection cell 112 comprises a third solid electrolyte layer 151 for detection made of zirconia having oxygen ion conductivity, and a fifth electrode 155 for detection and a sixth electrode 157 for reference disposed so as to sandwich the solid electrolyte layer 151 for detection. The electrode 155 for detection and the electrode 157 for reference are made of platinum or platinum alloy.

When the gas sensor element 10 is heated to the activation temperature (for example, 750° C.) and brought into an activated state, a first pump current Ip1 flowing into the first pump cell 111 is controlled by the sensor control device 50 so that voltage Vs applied to the electrodes of the oxygen concentration detection cell 112 stays at a pre-set constant voltage (for example, 425 mV). The first pump current Ip1 is generated as oxygen ions migrate in the first solid electrolyte layer 131 between the electrodes (between the first electrode 135 and the second electrode 137) in the first pump cell 111.

The gas sensor element 10 includes a second measurement chamber 161 to the rear (on the right in the drawing) of the first measurement chamber 159. A second diffusion resistor 117 made of a porous material is formed between the first measurement chamber 159 and the second measurement chamber 161. The second measurement chamber 161 is formed so that it penetrates through the oxygen concentration detection cell 112 in the lamination direction and the third electrode 145 of the second pump cell 113 is disposed therein.

In the gas sensor element 10, when a voltage is applied to the second pump cell 113 by the sensor control device 50, NOx present in the second measurement chamber 161 undergoes dissociation (reduction) due to the catalytic action of the third electrode 145 of the second pump cell 113. Then, a second pump current Ip2 begins to flow as oxygen ions obtained as the result of the dissociation migrate in the second solid electrolyte layer 141 between the electrodes (the third electrode 145 and the fourth electrode 147) in the second pump cell 113.

More specifically, the second pump cell 113 is configured so that second pump current Ip2 corresponding to the concentration of a particular gas component (NOx (oxides of nitrogen)) present in the second measurement chamber 161 flows between the electrodes (the third electrode 145 and the fourth electrode 147). The sensor control device 50 connected to the gas sensor element 10 is thus able to detect the NOx concentration on the basis of the magnitude and the integral value of the second pump current Ip2.

Referring to FIG. 1 again, the sensor control device 50 includes an Ip1 driver 51, a PID control circuit 52, an operational amplifier 53, an Rpvs measurement circuit 54, and an Ip2 driver 56.

The sensor control device 50 is connected to the first pump cell 111 of the gas sensor element 10 via a wire 42 and a wire 43, to the second pump cell 113 of the gas sensor element 10 via the wire 42 and a wire 44, and to the oxygen concentration detection cell 112 (Vs cell 112) of the gas sensor element 10 via a wire 41 and the wire 42.

The sensor control device 50 also includes an unillustrated output terminal, and the output terminal is connected to an analog input terminal of an unillustrated electronic control unit (hereinafter, also abbreviated as ECU) of the internal combustion engine. The electronic control unit (ECU) controls the respective portions of the internal combustion engine systematically, and performs various kinds of control processing, such as air-fuel ratio control and exhaust gas control of the internal combustion engine.

The sensor control device 50 outputs a voltage signal proportional to the magnitude of a current flowing into the first pump cell 111, a voltage signal proportional to the magnitude of a current flowing into the second pump cell 113, a voltage signal proportional to the voltage across the electrodes (between the electrodes Vs+ and Vs−) of the oxygen concentration detection cell 112, the voltage at each terminal of the gas sensor element 10, the internal resistance of the gas sensor element 10, and so forth to the ECU.

The Ip1 driver 51 is an operational amplifier used to drive Ip1 current into the first pump cell 111. The inverting input terminal (−) is connected to a Vcent terminal (potential reference terminal), the non-inverting input terminal (+) is connected to a reference potential output circuit 74, and the output terminal is connected to the Ip1+ terminal. The reference potential output circuit 74 outputs reference potential KVcent used as the reference in the sensor control device 50, and this output potential (several V) corresponds to the reference point target potential.

The first pump cell 111 of the gas sensor element 10 is connected onto the path from the Vcent terminal to the Ip1+ terminal via a Vs-/Ip-terminal, the wire 42, and the wire 43. The Ip1 driver 51 forms a negative feedback circuit due to this configuration, and therefore controls the Ip1 current in such manner that the potential of the Vcent terminal remains at the reference potential KVcent (the output potential of the reference potential output circuit 74).

The PID control circuit 52 controls the first pump current Ip1 in such a manner that the voltage (electromotive force Vs) across the electrodes of the oxygen concentration detection cell 112 (Vs cell 112) remains at the Vs control target value, referring to the potential of the Vcent terminal. The Vs control target value is output from a Vs control target value output circuit 73.

The PID control circuit 52 comprises a PID arithmetic circuit together with respective resistors and capacitors connected to a P1 terminal, to a P2 terminal, and to a P3 terminal serving as input and output signal lines of the sensor control device 50. The PID control circuit 52 performs a PID operation using the deviation, ΔVs, of the electromotive force Vs of the oxygen concentration detection cell 112 from the Vs control target value, and sets the potential of a Pout terminal so that the electromotive force Vs of the oxygen concentration detection cell 112 approaches the Vs control target value.

The Ip1 current is controlled through the control operation by the PID control circuit 52 and the control operation by the Ip1 driver 51 as described above.

More specifically, in a case where the electromotive force Vs of the oxygen concentration detection cell 112 is higher than the Vs control target value, the oxygen partial pressure in the first measurement chamber 159 is lower than the reference oxygen partial pressure. In such case, the PID control circuit 52 sets the potential of the Pout terminal so as to generate the Ip1 current that pumps in oxygen by means of the first pump cell 111 to make up for the shortfall of oxygen, through the PID calculation based on the deviation ΔVs.

On the other hand, in a case where the electromotive force Vs of the oxygen concentration detection cell 112 is lower than the Vs control target value, the oxygen partial pressure in the first measurement chamber 159 is higher than the reference oxygen partial pressure. In such a case, the PID control circuit 52 sets the potential of the Pout terminal so as to generate Ip1 current that pumps out excess oxygen by means of the first pump cell 111 through the PID calculation based on the deviation, ΔVs.

In addition, a constant current source circuit 72 of +several μA is connected to a Vs+ terminal, and the oxygen reference is generated by supplying an Icp current to the oxygen concentration detection cell 112 by this configuration.

The operational amplifier 53 connected between the Vs+ terminal and the PID control circuit 52 is part of a voltage follower circuit. Accordingly, because a high impedance is seen from the PID control circuit 52 side of the Vs+ terminal, the operational amplifier 53 restricts the flow of supply current from the constant current source circuit 72 of several +μA into the PID control circuit 52.

The Rpvs measurement circuit 54 measures the temperature of the gas sensor element 10 on the basis of internal resistance Rpvs of the oxygen concentration detection cell 112, and it comprises an operational amplifier, a resistor, a capacitor, and so forth. The Rpvs measurement circuit 54 gives rise to a change in voltage corresponding to the internal resistance value of the oxygen concentration detection cell 112, this value correlating with the element temperature when a specific current flows through the oxygen concentration detection cell 112 at a specific cycle. The Rpvs measurement circuit 54 then multiplies the resulting difference in voltage across the terminals of the oxygen concentration detection cell 112 by a constant number using an operational amplifier, and outputs a VRpvs voltage signal that varies within a range of 0 to 4.5 V. The VRpvs voltage signal is output to the unillustrated ECU.

When the Rpvs measurement circuit 54 sends the measurement current into the oxygen concentration detection cell 112, the Rpvs measurement circuit 54 disconnects the connection between the PID control circuit 52 and the operational amplifier 53 by driving a switch SW interposed between the PID control circuit 52 and the operational amplifier 53. In this manner, a change in voltage caused by the measurement current does not give rise to a change in an output of the PID control circuit 52. In other words, the Rpvs measurement circuit 54 measures the internal resistance Rpvs of the oxygen concentration detection cell 112, while the PID control circuit 52 and the operational amplifier 53 are disconnected by the switch SW.

The Ip2 driver 56 is an operational amplifier that is used to send the Ip2 current into the second pump cell 113. The non-inverting input terminal (+) is connected to a Vp2 setting circuit 57, the inverting input terminal (−) is connected to an Ip2/Vp2 terminal, and the output terminal is connected to the Ip2/Vp2 terminal via a detection resistor element 78 of the Ip2 current. In short, the Ip2 driver 56 controls the potential of the Ip2/Vp2 terminal so as to be equal to the output potential of the Vp2 setting circuit 57.

The Vp2 setting circuit 57 is provided to set the potential of the potential output terminal (the Ip2/Vp2 terminal) so that the voltage applied to the second pump cell 113 is the target applied voltage TVp2, referring to the Vcent terminal (potential reference terminal).

Figure 3:
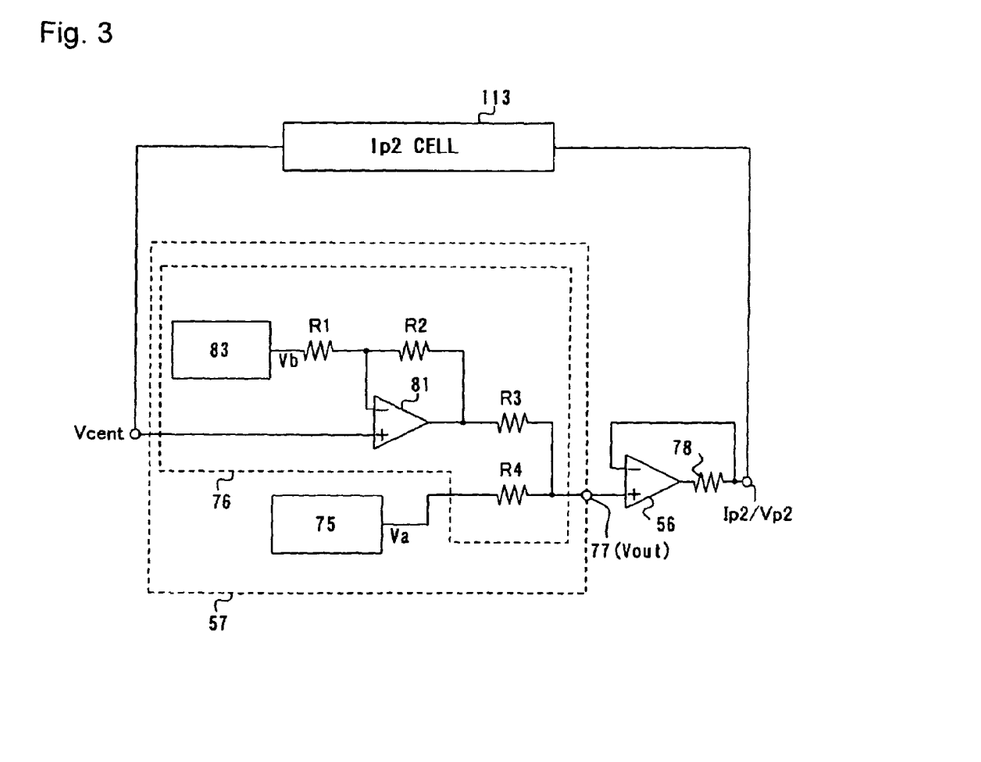
FIG. 3 is a circuit diagram of a Vp2 setting circuit connected to an Ip2 driver and a second pump cell.

The circuit diagram of the Vp2 setting circuit 57 is shown in FIG. 3.

In FIG. 3, connections with the Ip2 driver 56 and the second pump cell 113 in addition to the Vp2 setting circuit 57 are illustrated schematically.

As is shown in FIG. 3, the Vp2 setting circuit 57 includes a target potential output circuit 75 and an output point potential correction circuit 76.

The output potential (output point target potential Va) of the target potential output circuit 75 is set to be the potential of the potential output terminal (the Ip2/Vp2 terminal) when voltage applied to the second pump cell 113 is the target applied voltage TVp2, referring to the reference potential KVcent set to be the output potential (rated value) of the reference potential output circuit 74. The voltage value at which the second pump cell 113 changes to the state where NOx undergoes dissociation (reduction) is set to be the target applied voltage TVp2.

The output point potential correction circuit 76 includes an operational amplifier 81, first through fourth resistor elements R1 through R4, and a constant potential output circuit 83.

In the operational amplifier 81, the non-inverting input terminal (+) is connected to the Vcent terminal (potential reference terminal), the inverting input terminal (−) is connected to the constant potential output circuit 83 via the first resistor element R1, and the output terminal is connected to the non-inverting input terminal (+) of the Ip2 driver 56 via the third resistor element R3. The constant potential output circuit 83 outputs a constant potential Vb.

The first resistor element R1 is connected between the inverting input terminal (−) of the operational amplifier 81 and the constant potential output circuit 83, and the second resistor element R2 is connected between the inverting input terminal (−) and the output terminal of the operational amplifier 81.

The third resistor element R3 is connected between the output terminal of the operational amplifier 81 and an output terminal 77 of the Vp2 setting circuit 57. The fourth resistor element R4 is connected between the output terminal 77 and the output terminal of the target potential output circuit 75. The output terminal 77 is connected to the non-inverting input terminal (+) of the Ip2 driver 56.

In this embodiment, the resistance of the first resistor R1 is the same as the second resistor R2, while resistance of the third resistor R3 is the same as the fourth resistor R4.

In the Vp2 setting circuit 57 provided with the target potential output circuit 75 and the output point potential correction circuit 76 as described above, the potential of the output terminal 77 (the potential Vout after the Vp2 is corrected) is expressed by Mathematical Formula 1 below using the potential Vcent of the Vcent terminal, the output point target potential Va, and the constant potential Vb.

$$Vout = Vcent + \frac{Va}{2} - \frac{Vb}{2} \qquad \text{[Mathematical Formula 1]}$$

Because the Ip2 driver 56 controls the potential of the Ip2/Vp2 terminal so as to be equal to the potential (the potential Vout after the Vp2 is corrected) of the output terminal 77 of the Vp2 setting circuit 57, the potential of the Ip2/Vp2 terminal is set to be the potential Vout after the Vp2 is corrected.

The actual voltage Vp2 applied to the second pump cell 113 is determined according to the voltage difference between the potential of the Vcent terminal (potential reference terminal) and the potential of the Ip2/Vp2 terminal. If the voltage drop in a resistor element 79 connected between the Vs-/Ip-terminal and the Vcent terminal is a constant voltage value, Vd, then the voltage Vp2 applied to the second pump cell 113 can be expressed by Mathematical Formula 2:

$$Vp2 = Vout - Vcent - Vd \qquad \text{[Mathematical Formula 2]}$$

Mathematical Formula 3 is obtained by substituting the potential Vout after the Vp2 is corrected which is expressed by including Mathematical Formula 1 into Mathematical Formula 2.

$$Vp2 = \frac{Va}{2} - \frac{Vb}{2} - Vd \qquad \text{[Mathematical Formula 3]}$$

It is seen from Mathematical Formula 3 that because the voltage Vp2 applied to the second pump cell 113 (the voltage Vp2 across the terminals of the second pump cell 113) can be expressed by a constant value (the output point target potential Va, the constant potential Vb, and the constant voltage value Vd), it does not vary with the potential Vcent of the Vcent terminal (potential reference terminal).

As described above, the voltage Vp2 (the voltage Vp2 across the terminals of the second pump cell 113) applied to the second pump cell 113 does not vary with fluctuation in the potential of the Vcent terminal because the output point potential correction circuit 76 corrects the potential (the potential Vout after the Vp2 is corrected) of the output terminal 77 of the Vp2 setting circuit 57 in response to fluctuation in the potential of the Vcent terminal.

More specifically, when the potential of the Vcent terminal (potential reference terminal) becomes higher than the reference point target potential, the output point potential correction circuit 76 raises the potential of the output terminal 77 above the output point target potential Va by a quantity corresponding to the increase of the Vcent terminal potential. Conversely, when the potential of the Vcent terminal decreases below the reference point target potential, the output point potential correction circuit 76 lowers the potential of the output terminal 77 below the output point target potential Va by a quantity corresponding to the decrease in the Vcent terminal potential.

As described above, even when the potential of the Vcent terminal fluctuates (deviates from the reference potential KVcent) for any reason, the sensor control device 50 in the NOx detection device 1 is able to suppress fluctuation in the voltage Vp2 applied to the second pump cell 113 by correcting the potential of the Ip2/Vp2 terminal according to the fluctuation in Vcent terminal potential.

Hence, because the sensor control device 50 corrects the potential (output point target potential) of the output terminal 77 according to the fluctuation in potential of the Vcent terminal (potential reference terminal), even when the potential of the Vcent terminal (potential reference terminal) fluctuates due to the influence of noise and the like, it is possible to prevent the voltage Vp2 applied to the second pump cell 113 from deviating from the target applied voltage TVp2.

The sensor control device 50 is therefore able to suppress deterioration in control accuracy of voltage applied to the second pump cell 113 even where the potential of the Vcent terminal (potential reference terminal) fluctuates due to noise.

Figure 4:
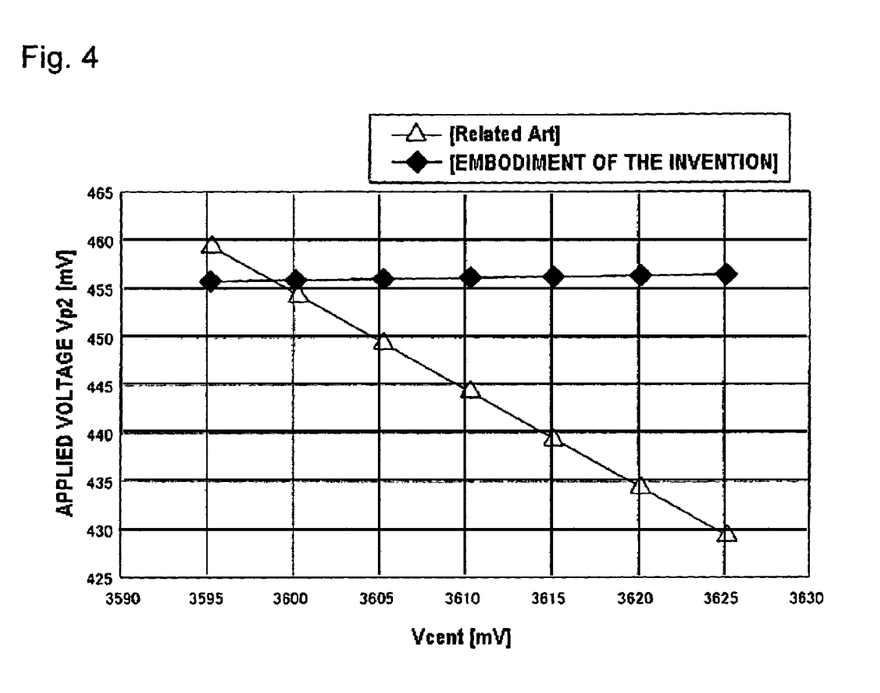
FIG. 4 is a view showing measurement results of the change in voltage applied to the second pump cell in response to fluctuation in the potential of a Vcent terminal (potential reference terminal) in the sensor control device according to one embodiment of the invention and a sensor control device of the related art.

The change of the voltage Vp2 applied to the second pump cell 113 in response to a fluctuation in the potential of the Vcent terminal (potential reference terminal) in the sensor control device 50 of this embodiment and that in a sensor control device of the related art were measured, and the measurement results are set forth in FIG. 4.

The sensor control device in the related art used for the measurement was built by replacing the Vp2 setting circuit 57 of the sensor control device 50 with the target potential output circuit 75 alone, so that the output terminal of the target potential output circuit 75 is connected to the non-inverting input terminal (+) of the Ip2 driver 56. In short, the sensor control device of the related art used for the measurement was built by eliminating the output point potential correction circuit 76 from the sensor control device 50 described above.

As is shown in FIG. 4, according to the measurement result of the sensor control device in the related art, the applied voltage Vp2 decreases as the potential Vcent of the Vcent terminal (potential reference terminal) becomes higher, and the voltage Vp2 applied to the second pump cell 113 therefore varies with a fluctuation in the potential of the Vcent terminal. In other words, in the sensor control device in the related art, because a fluctuation in the potential of the Vcent terminal is not corrected when the potential of the Ip2/Vp2 terminal is set, when the potential of the Vcent terminal fluctuates, the voltage Vp2 applied to the second pump cell 113 is different from the target applied voltage TVp2.

On the other hand, the measurement results of the sensor control device 50 of this embodiment confirm that the applied voltage Vp2 remains substantially constant even when the potential Vcent of the Vcent terminal (potential reference terminal) fluctuates. Thus, the voltage Vp2 applied to the second pump cell 113 hardly varies with a fluctuation in the potential of the Vcent terminal.

It is clear from the above measurement results that even when the potential of the Vcent terminal fluctuates, it is possible to suppress fluctuation in the voltage Vp2 applied to the second pump cell 113 with the sensor control device 50 of this embodiment.

In this embodiment, the sensor control device 50 corresponds to the sensor control device, the Vcent terminal corresponds to the potential reference terminal, the Ip2/Vp2 terminal corresponds to the potential output terminal, and the gas sensor element 10 (to be more specific, the second pump cell 113) corresponds to the sensor element. Also, the Ip1 driver 51 and the reference potential output circuit 74 correspond to the reference potential setting section, the Ip2 driver 56 and the target potential output circuit 75 correspond to the output potential setting section, and the output point potential correction circuit 76 corresponds to the output point potential correction section.

While one embodiment of the invention has been described, it should be apparent to those skilled in the art that the invention is not limited thereto, and that various changes in form and detail of the invention as shown and described above may be made. It is intended that such changes be included within the spirit and scope of the claims appended hereto.

For example, based on fluctuation in the potential of the Vcent terminal, not only may the potential of the Ip2/Vp2 terminal be corrected, but also the potential of the Vs+ terminal may be corrected.

To be more specific, the sensor control device 50 applies a voltage not only to the second pump cell 113, but also to the oxygen concentration detection cell 112, and the voltage Vs applied to the oxygen concentration detection cell 112 is determined according to the difference between the Vcent terminal (potential reference terminal) potential and the Vs+ terminal potential. Hence, by providing a Vs output point potential correction circuit that corrects the potential of the Vs+ terminal according to a fluctuation in the potential of the Vcent terminal (potential reference terminal), it is possible to suppress fluctuation in the voltage applied to the oxygen concentration detection cell 112 even when the potential of the Vcent terminal (potential reference terminal) fluctuates.

The sensor control device configured as described above has plural potential output terminals and plural output potential setting sections and output point potential correction sections corresponding to the plural potential output terminals. The sensor control device configured as described above is able to apply a voltage to each cell in a gas sensor element provided with plural cells that requires an external voltage, and is also able to suppress fluctuation in the voltage applied to each cell induced by a fluctuation at the Vcent terminal (potential reference terminal).

In the sensor control device configured as described above, the Vcent terminal corresponds to the potential reference terminal, and the Ip2/Vp2 terminals and the Vs+ terminals correspond to the plural potential output terminals. Also, the output point potential correction circuits 76 and the Vs output point potential correction circuits correspond to the plural output point potential correction sections, the Ip2 drivers 56 and the target potential output circuits 75 correspond to the plural output potential setting sections, and the PID control circuits 52 and the Vs control target value output circuits 73 correspond to the plural output potential setting sections.

The sensor element to be controlled is not limited to the NOx sensor element described above, and for example, it may be any sensor element configured to include a single cell that requires voltage control such as a UEGO sensor (Universal Exhaust Gas Oxygen sensor). Further, the sensor element is not limited to a gas sensor element for detecting a gas, and the sensor control device of the invention is able to control any sensor that measures a subject when an external voltage is applied, such as a temperature sensor, a humidity sensor, and a load sensor.

This application is based on Japanese Patent Application No. 2005-320916 filed Nov. 4, 2005, the disclosure which is incorporated herein by reference in its entirety.

What is claimed is:

1. A sensor control device including a potential reference terminal and a potential output terminal, said sensor control device being adapted for applying a voltage to a sensor element having an oxygen ion conductor and a pair of electrodes formed on the oxygen ion conductor and for connecting the potential reference terminal to one of the pair of electrodes and the potential output terminal to the other of the pair of electrodes, said sensor control device comprising:

a reference potential setting section for setting the potential of the potential reference terminal to a reference point target potential;

an output potential setting section for setting the potential of the potential output terminal to an output point target potential so that a target voltage is applied to the sensor element with reference to the potential of the potential reference terminal set to the reference point target potential; and an output point potential correction section for correcting the output point target potential so that the voltage applied to the sensor element remains at the target applied voltage independent of fluctuation in the potential of the potential reference terminal, said output potential setting section adjusting the potential of the potential output terminal so as to assume the corrected output point target potential.

2. The sensor control device according to claim 1, wherein the output point potential correction section comprises a non-inverting amplifier circuit having an input, and the potential of the potential reference terminal is applied to the input of the non-inverting amplifier.

3. The sensor control device according to claim 1, comprising plural potential output terminals, and plural output potential setting sections and plural output point potential correction sections corresponding to the respective plural potential output terminals.

4. A gas sensor and a sensor control device for applying a voltage to a sensor element of the gas sensor, said gas sensor comprising:

a first measurement chamber into which a gas to be measured is introduced via a first diffusion resistor portion;

a first oxygen ion pump cell comprising a first oxygen ion conductor and first and second electrodes formed on the first oxygen ion conductor so that the first electrode is arranged in the first measurement chamber for pumping oxygen into or out of the gas to be measured that has been introduced into the first measurement chamber;

a second measurement chamber into which the gas to be measured after having been acted on in the first measurement chamber is introduced via a second diffusion resistor portion;

a second oxygen ion pump cell comprising a second oxygen ion conductor and third and fourth electrodes formed on the second oxygen ion conductor so that the third electrode is arranged in the second measurement chamber, wherein a current corresponding to the concentration of a particular gas in the second measurement chamber flows in the second oxygen ion pump cell;

a reference oxygen chamber set to have a reference oxygen partial pressure atmosphere; and an oxygen partial pressure detection cell comprising a third oxygen ion conductor and fifth and sixth electrodes formed on the third oxygen ion conductor so that the fifth electrode is arranged in the first measurement chamber and the sixth electrode is arranged in the reference oxygen chamber;

said sensor control device comprising a potential output terminal and a potential reference terminal electrically connected to said third and fourth electrodes of the second oxygen ion pump cell, respectively, or to said fifth and sixth electrodes of the oxygen partial pressure detection cell, respectively, said sensor control device further comprising:

a reference potential setting section for setting the potential of the potential reference terminal to a reference point target potential;

an output potential setting section for setting the potential of the potential output terminal to an output point target potential so that a target voltage is applied to the sensor element with reference to the potential of the potential reference terminal set to the reference point target potential; and an output point potential correction section for correcting the output point target potential so that the voltage applied to the sensor element remains at the target applied voltage independent of fluctuation in the potential of the potential reference terminal, said output potential setting section adjusting the potential of the potential output terminal so as to assume the corrected output point target potential.

5. The gas sensor and sensor control device for applying a voltage to a sensor element of the gas sensor as claimed in claim 4, wherein the potential output terminal and the potential reference terminal are electrically connected to the third and fourth electrodes of the second oxygen ion pump cell, respectively.

6. The gas sensor and sensor control device for applying a voltage to a sensor element of the gas sensor as claimed in claim 4, wherein the potential output terminal and the potential reference terminal are electrically connected to the fifth and sixth electrodes of the oxygen partial pressure detection cell, respectively.

7. The gas sensor and sensor control device for applying a voltage to a sensor element of the gas sensor as claimed in claim 4, wherein the output point potential correction section comprises a non-inverting amplifier circuit having an input, and the potential of the potential reference terminal is applied to the input of the non-inverting amplifier.

8. The gas sensor and sensor control device for applying a voltage to a sensor element of the gas sensor as claimed in claim 4, said sensor control device comprising plural potential output terminals, and plural output potential setting sections and plural output point potential correction sections corresponding to respective plural potential output terminals.

9. The gas sensor and sensor control device for applying a voltage to a sensor element of the gas sensor as claimed in claim 8, wherein individual ones of said plural potential output terminals are separately connected to at least the third electrode of the second oxygen ion pump cell and the fifth electrode of the oxygen partial pressure detection cell.

10. The sensor control device according to claim 1, wherein the voltage applied to the sensor element does not vary with fluctuation in the potential of the potential reference terminal.

11. The sensor control device according to claim 4, wherein the voltage applied to the sensor element does not vary with fluctuation in the potential of the potential reference terminal.

* * * * *